(12) United States Patent
Chang

(10) Patent No.: US 10,842,002 B2
(45) Date of Patent: Nov. 17, 2020

(54) HEAD-MOUNTED MEDICAL/DENTAL ACCESSORIES WITH VOICE-CONTROLLED OPERATION

(71) Applicant: General Scientific Corporation, Ann Arbor, MI (US)

(72) Inventor: Byung J. Chang, Ann Arbor, MI (US)

( * ) Notice: Subject to any disclaimer, the term of this patent is extended or adjusted under 35 U.S.C. 154(b) by 84 days.

(21) Appl. No.: 16/017,778

(22) Filed: Jun. 25, 2018

(65) Prior Publication Data

US 2018/0310384 A1    Oct. 25, 2018

Related U.S. Application Data

(63) Continuation-in-part of application No. 15/136,380, filed on Apr. 22, 2016, now Pat. No. 10,066,816,
(Continued)

(51) Int. Cl.
*H05B 47/12*    (2020.01)
*G10L 15/22*    (2006.01)
(Continued)

(52) U.S. Cl.
CPC ............ *H05B 47/12* (2020.01); *A61B 90/30* (2016.02); *A61B 90/35* (2016.02); *A61B 90/361* (2016.02); *F21L 4/00* (2013.01); *F21V 21/084* (2013.01); *F21V 23/02* (2013.01); *F21V 23/04* (2013.01); *F21V 23/0471* (2013.01); *G06F 3/167* (2013.01); *G10L 15/22* (2013.01); *H04N 5/232* (2013.01); *H04N 5/23216* (2013.01); *H05B 45/10* (2020.01); *A61B 2017/00203* (2013.01); *A61B 2017/00207* (2013.01);
(Continued)

(58) Field of Classification Search
CPC ..... H05B 37/0236; G06F 3/167; A61B 90/30; A61B 2090/502; A61B 2017/00203; G10L 15/22; G10L 2015/223; F21V 21/084; F21V 33/0052; H04N 5/23296
See application file for complete search history.

(56) References Cited

U.S. PATENT DOCUMENTS 6,289,140 B1 * 9/2001 Oliver ................. G10L 15/30
                                                      382/313
2005/0134439 A1 * 6/2005 Moore ............... A42B 3/0453
                                                      340/432
(Continued)

*Primary Examiner* — Evan P Dzierzynski
(74) *Attorney, Agent, or Firm* — The Law Offices of John G. Posa

(57) ABSTRACT

Head-mounted accessories for surgeons and medical/dental practitioners are equipped with no-touch, hands-free controls. A voice-activated headlamp includes a controller operative to send a signal to control a light source in accordance with a voice command received through an integrated or remote microphone. The voice command and control may be speaker-dependent or speaker-independent, and the head-mounted unit may include an interface to a computer for voice-command training or other purposes. The head-mounted unit includes a memory for storing the voice commands. The invention may be used to control other medical/dental accessories such as a head-mounted video camera, in which case the controller is further operative to at least turn the video camera ON or OFF. More preferably, a controller is additionally operative to control the focus or zoom of the video camera in accordance with a voice command.

34 Claims, 7 Drawing Sheets

Related U.S. Application Data which is a continuation-in-part of application No. 14/302,899, filed on Jun. 12, 2014, now abandoned, which is a continuation-in-part of application No. 13/929,394, filed on Jun. 27, 2013, now abandoned.

(51) Int. Cl.

| | |
|---|---|
| F21V 23/04 | (2006.01) |
| F21V 23/02 | (2006.01) |
| F21V 21/084 | (2006.01) |
| A61B 90/35 | (2016.01) |
| A61B 90/00 | (2016.01) |
| H04N 5/232 | (2006.01) |
| F21L 4/00 | (2006.01) |
| G06F 3/16 | (2006.01) |
| A61B 90/30 | (2016.01) |
| H05B 45/10 | (2020.01) |
| F21Y 115/10 | (2016.01) |
| F21V 33/00 | (2006.01) |
| G02C 11/04 | (2006.01) |
| F21V 23/00 | (2015.01) |
| A61B 17/00 | (2006.01) |
| A61B 90/50 | (2016.01) |

(52) U.S. Cl.
CPC ........... *A61B 2017/00734* (2013.01); *A61B 2090/309* (2016.02); *A61B 2090/3616* (2016.02); *A61B 2090/502* (2016.02); *F21V 23/003* (2013.01); *F21V 33/0052* (2013.01); *F21Y 2115/10* (2016.08); *G02C 11/04* (2013.01); *G10L 2015/223* (2013.01); *H04N 5/23212* (2013.01); *H04N 5/23296* (2013.01)

(56) References Cited

U.S. PATENT DOCUMENTS

| | | | | |
|---|---|---|---|---|
| 2009/0073694 | A1* | 3/2009 | Scannell, Jr. | F21S 6/005 362/253 |
| 2010/0245585 | A1* | 9/2010 | Fisher | H04M 1/6066 348/164 |
| 2011/0145978 | A1* | 6/2011 | Harbin | A61B 90/35 2/209.13 |
| 2012/0120636 | A1* | 5/2012 | Wilt | A61B 90/11 362/105 |
| 2014/0119569 | A1* | 5/2014 | Peeler | G06F 3/016 381/94.1 |
| 2014/0191664 | A1* | 7/2014 | Johnson | H05B 33/0857 315/152 |
| 2016/0091188 | A1* | 3/2016 | Milligan | A42B 3/044 362/105 |
| 2017/0127746 | A1* | 5/2017 | Pietrzak | A42B 3/042 |
| 2018/0109930 | A1* | 4/2018 | Kim | H04W 88/06 |

* cited by examiner

HEAD-MOUNTED MEDICAL/DENTAL ACCESSORIES WITH VOICE-CONTROLLED OPERATION

REFERENCE TO RELATED APPLICATIONS

This application is a continuation-in-part of U.S. patent application Ser. No. 15/136,380, filed Apr. 22, 2016, which is a continuation-in-part of U.S. patent application Ser. No. 14/302,899, filed Jun. 12, 2014, which is a continuation-in-part of U.S. patent application Ser. No. 13/929,394, filed Jun. 27, 2013, the entire content of all of these applications being incorporated herein by reference.

FIELD OF THE INVENTION

This invention relates generally to headlights and other accessories used by surgeons, medical and dental practitioners and, in particular, to such accessories with no-touch, hands-free controls.

BACKGROUND OF THE INVENTION

It is common for surgeons and medical/dental practitioners to wear headlights to enhance vision. Typical headlights using light-emitting diodes and optical fibers may be found at http://surgitel.com/headlights.

With such systems, the headlight contains only the light source and beam-forming optics. The power supply is disposed remotely, and may be belt-worn, for example.

One of the problems with existing systems is that the control unit may not be sterilized, such that the practitioner's hand may become contaminated if the light is turned ON or OFF during a procedure.

SUMMARY OF THE INVENTION

This invention resides in head-mounted accessories for surgeons and medical/dental practitioners with no-touch, hands-free controls. One embodiment is directed to a voice-activated headlamp comprising a battery unit and a head-mounted unit. The head-mounted unit includes a light source, a power switch receiving power from the battery unit, a microphone, and a controller operative to send a signal to the power switch to control the light source in accordance with a voice command received through the microphone. According to a preferred embodiment, the voice command at least includes turning the light source ON or OFF.

The microphone may be mounted on the head-mounted unit, or the head-mounted unit may include an interface for communication with one or more remote microphones. The battery unit may be physically coupled directly to the head-mounted unit, or the head-mounted unit may include an interface for receiving power from a remote battery unit.

The voice command and control may be speaker-dependent or speaker-independent, and the head-mounted unit may include an interface to a computer for voice-command training or other purposes. The head-mounted unit includes a memory for storing the voice commands.

The invention may be used to control other medical/dental accessories such as a head-mounted video camera, in which case the controller is further operative to at least turn the video camera ON or OFF. More preferably, a controller is additionally operative to control the focus or zoom of the video camera in accordance with a voice command.

In preferred embodiments, the battery unit provides fixed-voltage power signals to the head-mounted unit such that no control signals are required from the head-mounted unit to the battery unit. The power switch may be a field-effect transistor (FET), and may receive a fixed-voltage power signal directly from the battery unit. The invention preferably further includes a mechanism to attach the head-mounted unit to eyeglass frames or to a headband.

A proximity sensor may be provided to control the light source or assist in setting an ON or OFF threshold of the light source. For example, an infrared (IR) motion sensor may be used to turn the light source ON and OFF is response to the detection of a hand or other body part by the sensor without or without voice control. The proximity sensor is an active infrared (IR) sensor including an IR emitter and an IR detector.

A mechanism may be provided to attach the IR sensor to clothing, the IR sensor to the eyeglass frames, the headband, or the light source. The light source and IR sensor may be interconnected to an electrical coupler through separate cables, with a combination cable being used to interconnect the light source and IR sensor to the power supply and control unit through a single combination cable. The preferred embodiment includes an adjustable-proximity ON/OFF control enabling the activation distance to be customized for different user preferences.

DETAILED DESCRIPTION OF THE INVENTION

This invention is directed to a headlight with an infrared sensor enabling the light to be turned ON and OFF without physical contact. As such, the invention is ideally suited for surgical, medical and dental applications wherein a sterile field may be compromised through manual contact. While in the preferred embodiments the light source comprises one or more light-emitting diodes (LEDs), the invention is not limited in terms of the light source used.

Figure 1:
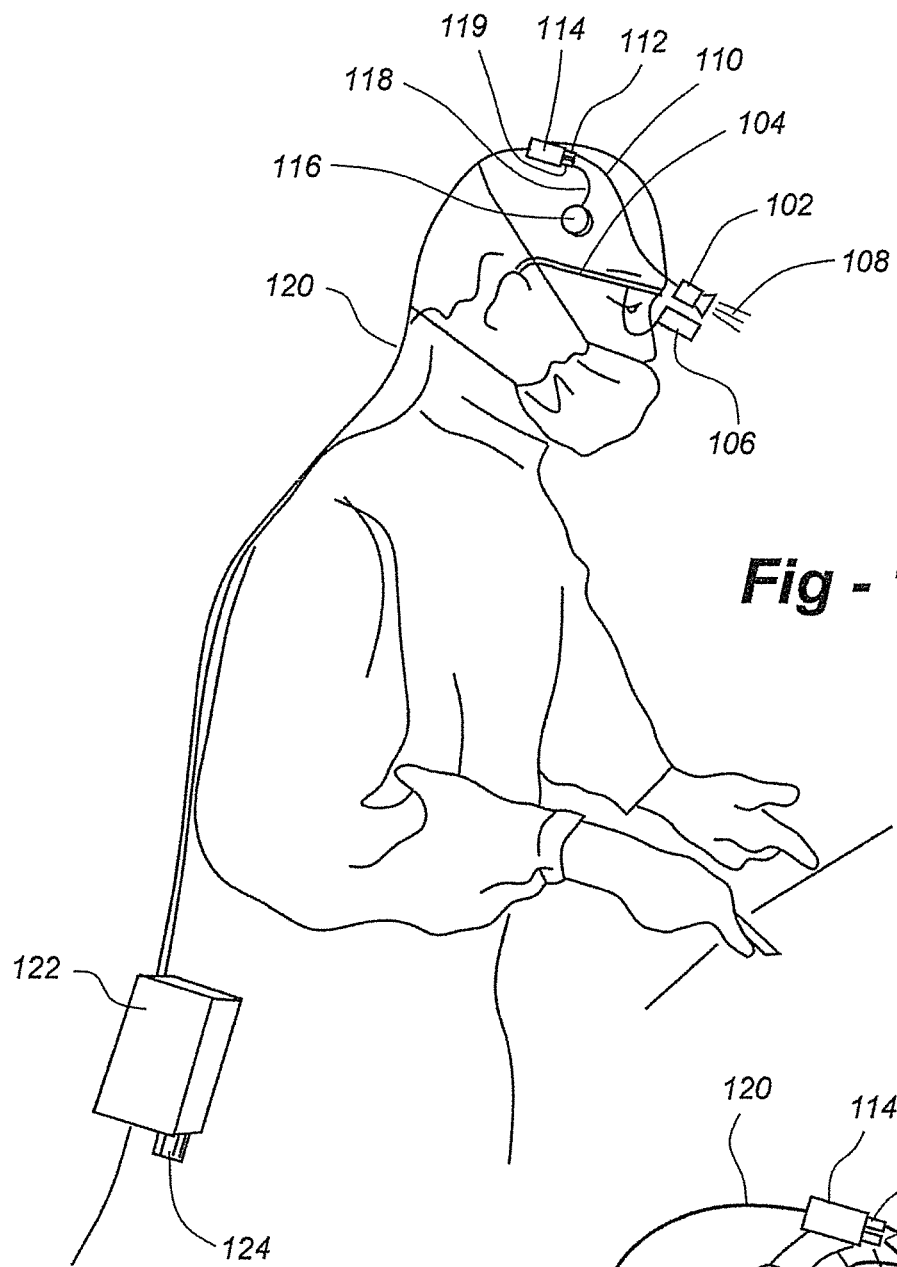
FIG. 1 is a drawing of an embodiment of the invention using an eyeglass frame mounted headlight.

FIG. 1 is a drawing of an embodiment of the invention using an LED headlight 102 mounted to eyeglass frames 104. In all embodiments, the light source may be permanently connected or temporarily coupled by way of a clip-on structure. Loupes 106, either the flip-up type or through-the-lens (TTL) type may be provided in conjunction with light source 102.

The light source 102 includes beam-forming and/or focusing optics (not shown) to produce a desired beam pattern 108. The LED(s) are powered through cable 110 which is ultimately connected to remote power supply and controller 122, which may be belt-worn, through combination cable 120. The system also includes an infrared (IR) sensor module 116 that is also coupled to the power supply and controller 122 through combination cable 120.

While the light 102 and IR sensor may be connected to the unit 122 directly, in the preferred embodiment, cable 110 from the light connects to a coupling unit 114 through electrical connector 112, and cable 118 from the sensor connects to the coupling unit 114 through electrical connector 119, enabling either or both of the cables 110, 118 to be disconnected. The power supply and control unit 122 contains rechargeable batteries that are replenished via connect to a changer shown in the block diagram of FIG. 3. A manual control knob 124 may be provided to establish a desired level of brightness prior to ON/OFF control using the IR sensor.

IR sensor 116 is preferably a miniature passive IR sensor available from various suppliers. For example, the KC7783 PIR Sensor Module is a pyroelectric sensor module developed for human body part detection. A PIR detector, combined with a Fresnel lens, are mounted on a compact printed circuit board together with an analog IC (the KC778B) providing a TTL output that can be directly connected to a microcontroller or logic device disposed in remote unit 122. Again, this PIR sensor is one of many applicable to the invention.

Figure 2:
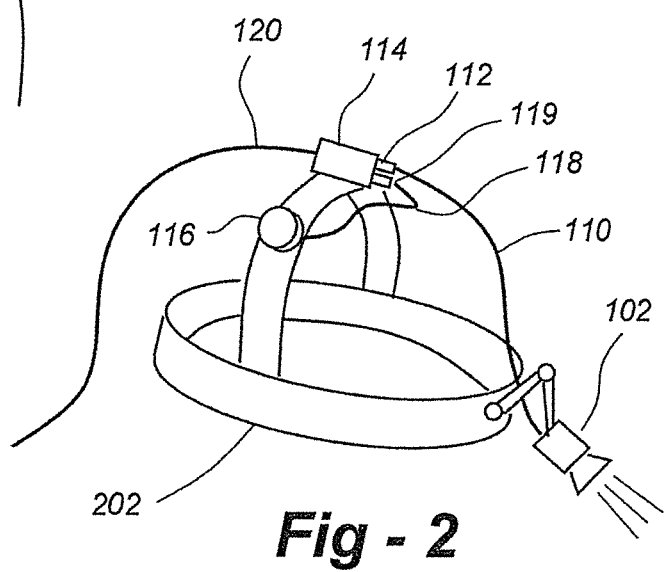
FIG. 2 is a drawing of an embodiment of the invention using headband-mounted headlight.

The IR sensor may be mounted at any convenient location, though in the preferred embodiment, it is head-mounted, whether clipped to a head mask or other clothing, mounted on eyeglass frames, the light source itself, or a headband 202 of the type depicted in FIG. 2. The sensor is preferably oriented in a direction that is least likely to experience false activation from bright/warm lights, other individuals, and so forth.

In operation, a user waves their hand in the proximity of the sensor 116, which causes the light 102 to turn ON and OFF without physical contact. In the preferred embodiment, the detection distance of the sensor is adjusted to be on the order of about 5 to 10 cm to enhance proper operation. This activation distance, as well as the field of view, may be adjusted through electrical component selection and/or sensor lens optics, materials, translucency, and so forth.

Figure 3:
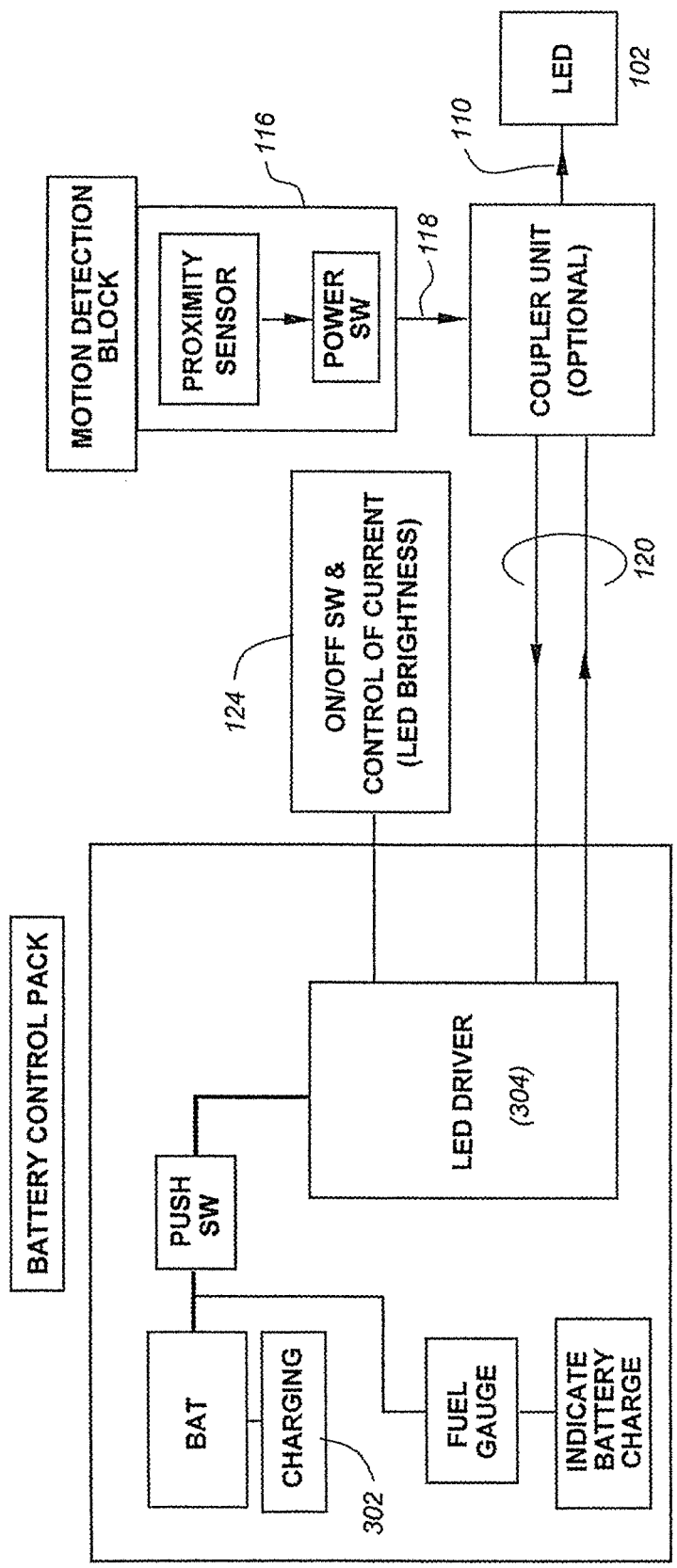
FIG. 3 is a block diagram of the invention showing cables, light emitter, and sensor.

Referring to FIG. 3, the electrical circuitry 304 in the power supply and control unit 122 may be designed to simply toggle the light ON/OFF with each hand/body part detection. In other words, if the light is ON, the user waves their hand to turn it OFF and vice-versa. Further, if the light is ON or OFF by mistake, one wave of the hand resents the light to the correct activation.

Figure 4:
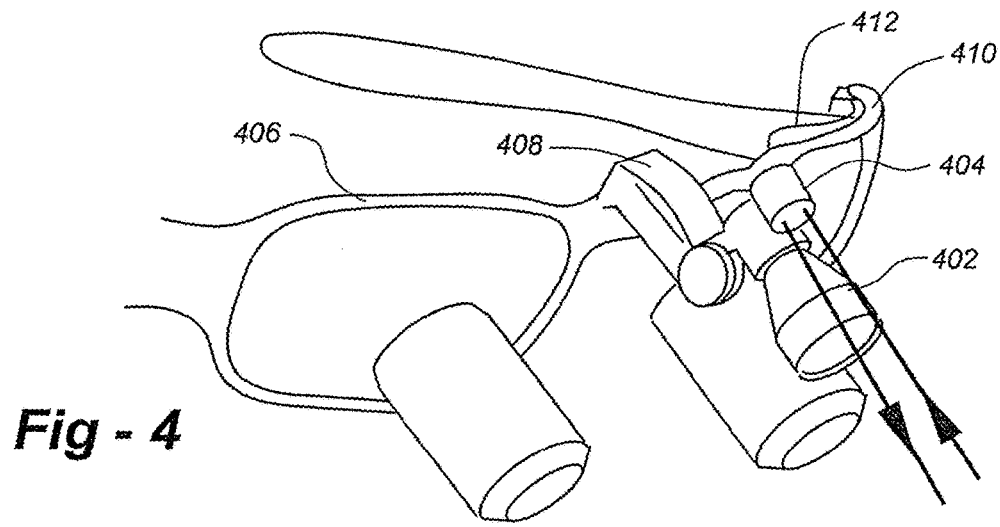
FIG. 4 is a drawing that illustrates an embodiment of the invention using an active IR sensor with a variable threshold to customize the activation distance.

FIG. 4 is a drawing that illustrates an embodiment of the invention using an active optical proximity sensor with a variable threshold to customize the activation distance. The sensor is mounted in a housing 404 which includes a light emitter and detector described in further detail below. The housing 402 is an LED light source which is coupled to eyeglass frames 406 through mechanically adjustable coupler 408. The frames 406 are shown with through-the-lens loupes though the invention is not limited by the choice of loupes, coupler or particular light unit. The optical orientation of the optical proximity sensor is preferably aligned with the optical axis of light 402 though this is also not necessary as a user may desire sidewise control. Cable 410 is routed to a power source and control unit for the headlamp 404, whereas cable 412 is routed to a separate power source and control unit for the proximity detector 404.

Figure 5:
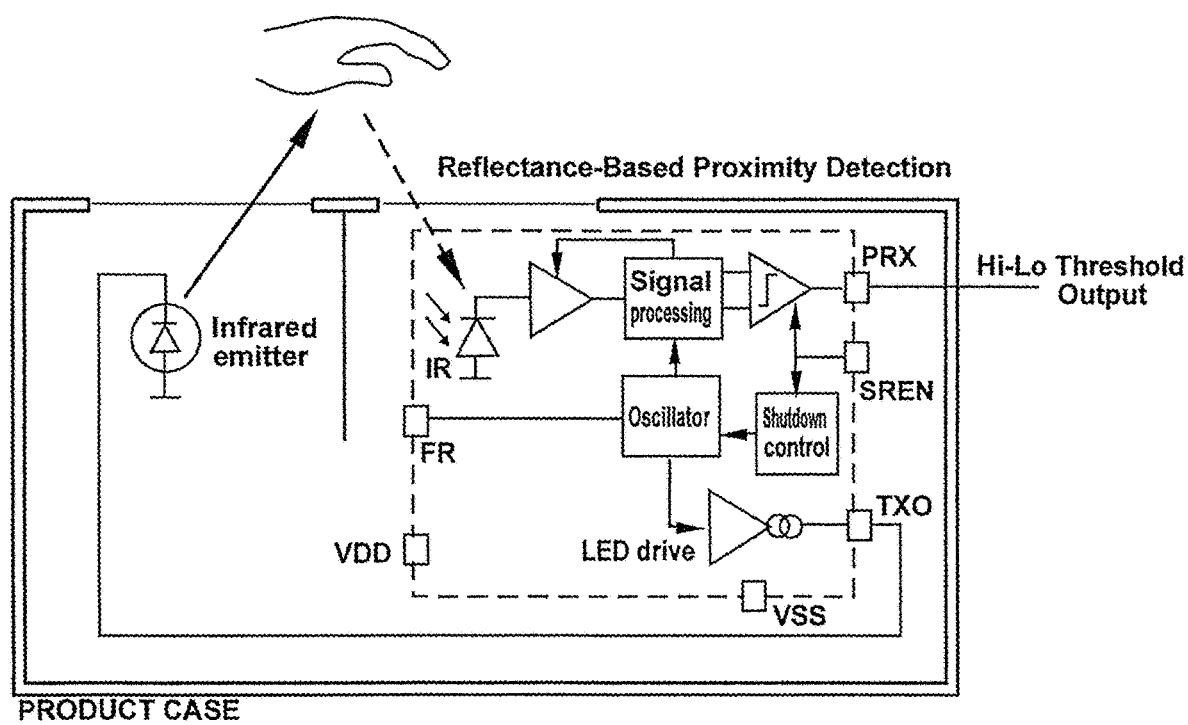
FIG. 5 is a block diagram of an optical proximity detector applicable to the invention.
Figure 6:
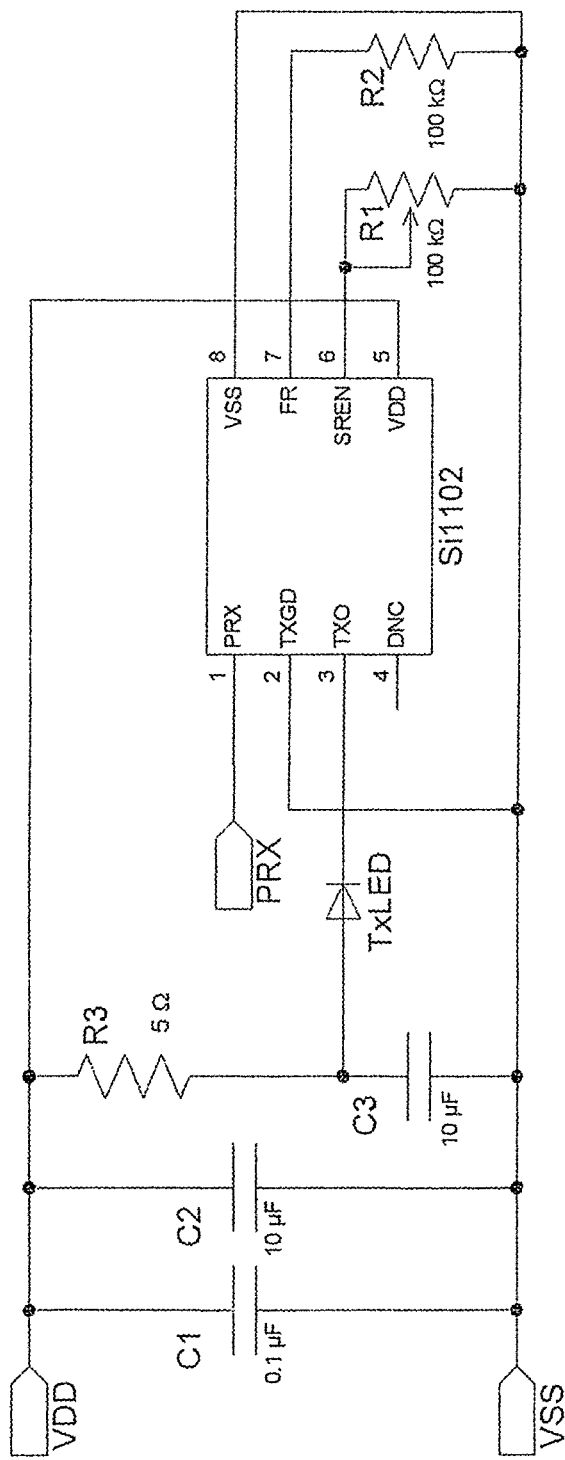
FIG. 6 is a schematic depicting how the detector of FIG. 5 may be implemented.

FIG. 5 is a block diagram of the optical proximity detector, which in this case happens to be a Si1102 device made by Silicon Labs. Comparable units from other manufacturers may be substituted. FIG. 6 is a schematic depicting how the detector of FIG. 5 may be implemented. The Si1102 is an active optical reflectance proximity detector with a simple on/off digital output whose state is based upon the comparison of reflected light against a set threshold. An LED sends light pulses whose reflections reach a photodiode and are processed by the Si1102's analog circuitry. If the reflected light is above the detection threshold, the Si1102 asserts the active-low PRX output to indicate proximity. The potentiometer, R1, is used to set the proximity detection threshold. The Si1102 periodically detects proximity at a rate that can be programmed by a single resistor (R2). Although the thresholds are normally set using a potentiometer for R1 (or R2), it is possible to digitally control various resistance values by using MCU GPIO pins to switch-in different value resistors (or parallel combinations of resistors). Regardless of which resistor(s) are used to control activation proximity, they may be located on unit 404 or remotely in the power supply/control unit for the sensor unit. In the preferred embodiment, a user is able to adjust the ON/OFF proximity of a hand, for example, to be in the range of one to 12 inches or more.

Figure 7:
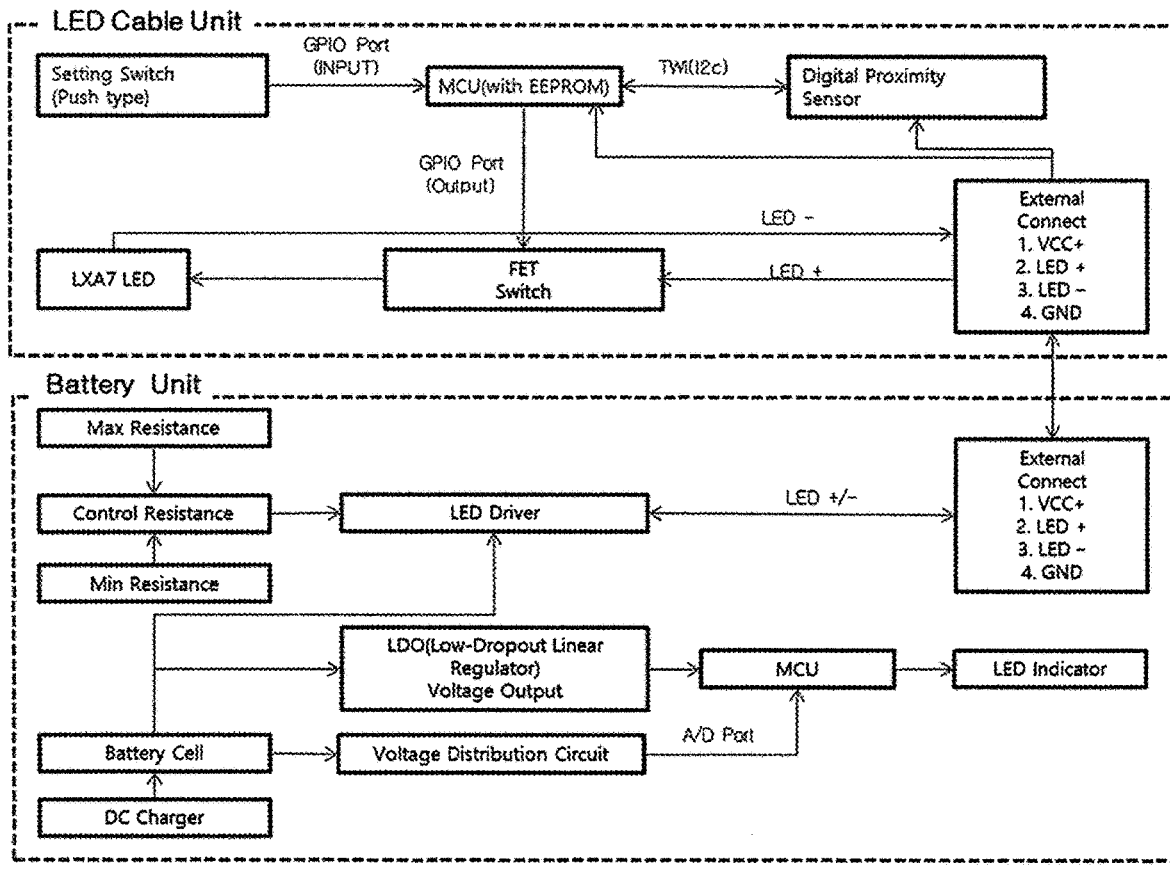
FIG. 7 is a block diagram of a microprocessor-based (MCU) version of a motion-activated LED headlamp controller with proximity adjustment.

FIG. 7 is a block diagram of a microprocessor-based (MCU) version of a motion-activated LED headlamp controller with proximity adjustment. All of the electronics associated with proximity control of the LED is disposed in the LED Cable Unit, such that only power at fixed voltages needs be delivered to the LED Cable Unit through a single cable from the Battery Unit. In particular, an External Connect in the Battery Unit delivers LED +/− at a fixed voltage as well as VCC+ and ground to power the MCU and other components in the LED Cable Unit, also at a fixed voltage. As with other embodiments disclosed herein, by placing all proximity ON/OFF and threshold controls at the location of the LED light source, no feedback or control signals need to be routed from the LED Cable Unit back to the Battery Unit. Thus, in the configuration of FIG. 4, only a single power cable needs to be routed from the Battery Unit to the sensor 404 and LED source 402.

In the block diagram of FIG. 7, an EEPROM associated with the MCU stores the threshold value enabling the Proximity Sensor (PS) to turn the FET Switch (and LED light) ON and OFF. If the signal from the PS becomes stronger than the stored threshold value, the MCU is operative to turn the FET and LED ON and OFF. If a user desires a different activation distance, they can replace the existing threshold value using the pushbutton Setting Switch. When this reset button is pushed, the MCU detects the signal reflected from an object (such as hand) at a desired activation distance and stores this new criteria value in the EEPROM of the MCU. The resetting function will allow users to decide their desirable activation distance.

Figure 8:
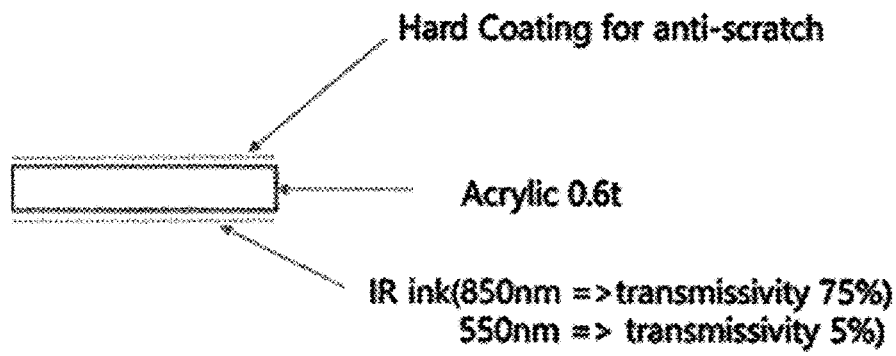
FIG. 8 is a cross section of an absorption-type IR filter applicable to the invention.

The LED light source includes an internal IR LED (about 900 nm), with IR filters being used to block stray IR signals from outside light sources such as room lights and dental or surgical overhead lights. Applicable IR filters have a high transmissivity for the internal IR wavelength and the low transmissivity for other wavelengths. Without the use of such filters the signal detection distance may vary significantly. FIG. 8 is a cross section of an absorption-type IR filter applicable to the invention, with the understanding that other types of filters may be used so long as they have a high transmissivity for the internal IR wavelength and the low transmissivity for other wavelengths.

Figure 9:
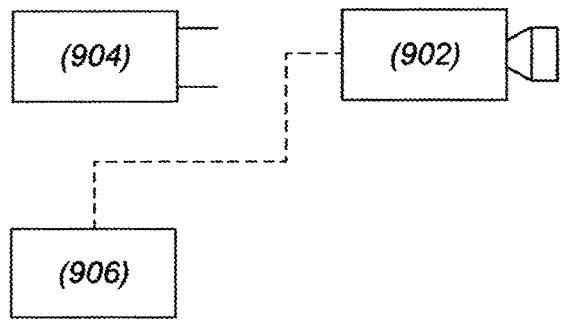
FIG. 9 shows how a head-mounted unit may be interconnected to a remote battery unit and/or a directly coupled rechargeable battery unit, resulting in a wireless, entirely self-contained head-mounted unit.

As shown in FIGS. 3 and 7, an advantage of embodiments of the invention is that only power and ground wires are required between a remote battery unit and the head-mounted unit, thereby eliminating the need for control signals to be routed to the battery unit. Another advantage is that the power supply need not be remote, and may be physically coupled directly to the head-mounted unit. As shown in FIG. 9, the same head-mounted unit 902 may accept a physically coupled rechargeable battery pack 904, or may be connected to a remote source 906, as previously described. The attachment of battery 904 converts the system into a completely wireless head-mounted light.

Particularly when the LED brightness control is located on the remote battery unit, it may be advantageous to run multiple power lines (plus ground) from the battery unit to the head-mounted unit, as this allows dimming with a separate power line being used to control lower-current circuitry in the head-mounted unit. However, if brightness control is not provided or desired, only two wires are needed from the power supply to the head-mounted unit, one for power and one for ground. In this configuration, power to control electronic circuitry made be derived from the same line used to power the LEDs, with a suitable power supply. As a further alternative, brightness control may be provided in the head-mounted unit, again requiring only power and ground from the battery pack, whether remote or coupled to the head-mounted unit.

Figure 10:
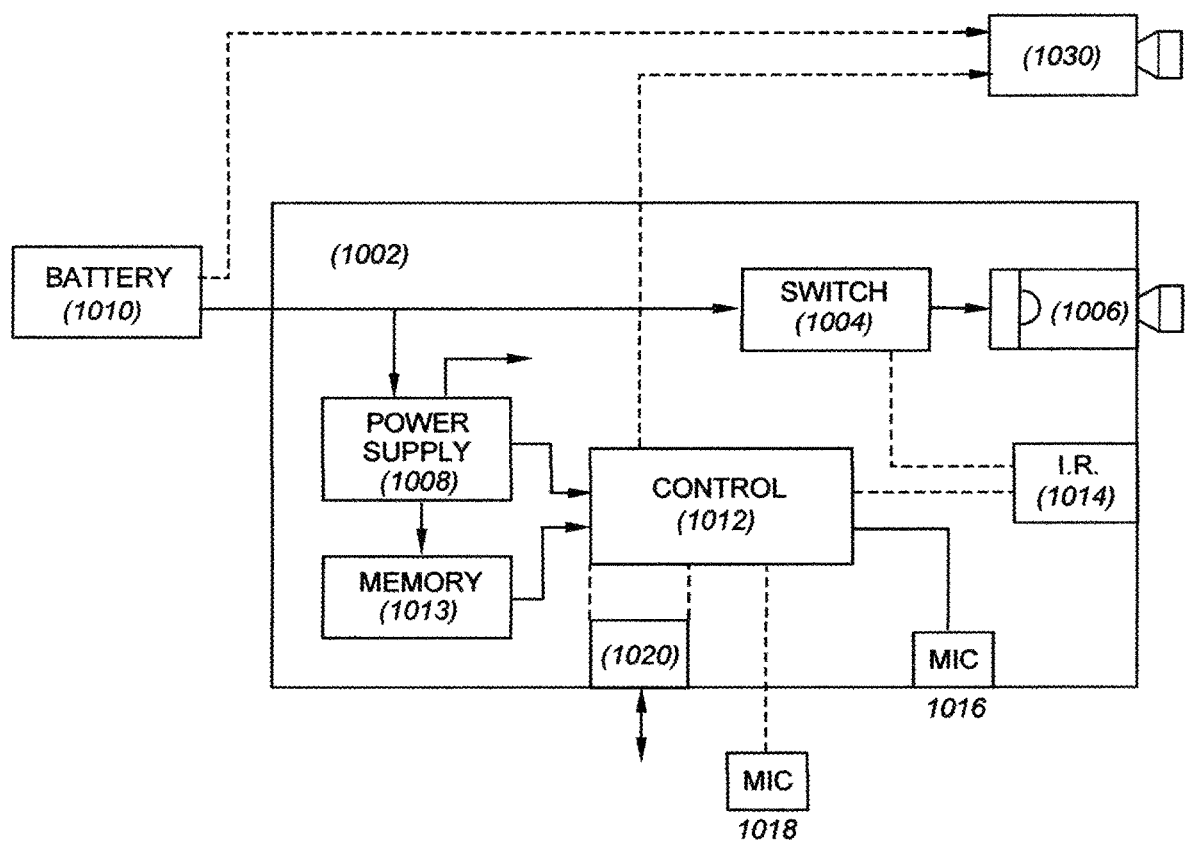
FIG. 10 is a block diagram showing important components associated with a voice-activated embodiment of the invention.

In alternative embodiments of the invention, voice control may be used instead of, or in conjunction with, infrared sensing. FIG. 10 illustrates an embodiment of the invention that includes speech recognition and voice command control. The head-mounted unit, 1002, preferably includes a power switch 1104 used to route power from rechargeable battery supply 1010 to light emitter(s) 1006. Again battery unit 101 may be remote or physically coupled to the head-mounted unit 1002. If separate power lines are not provided from the battery unit 1010, a power supply 1008 may be used to power electronic circuits in the head-mounted unit 1002, such as a microcontroller 1012. The microcontroller 1012 may be of conventional available design, and may have an internal memory or separate memory 1013 for storing command-related programs.

A passive or active infrared sensor 1014 may be provided to control switch 1004, though voice recognition is preferably used instead. Those of skill will appreciate that voice control may be provided in the form of a separate integrated circuit or module, as available from numerous sources such as Sensory, Inc. of Santa Clara, Calif., or software may be provided for execution by controller 1012. Again, such software is also available from various sources. A wired or wireless interface 1020 to a computer may be provided for programming purposes. The voice recognition may be speaker-independent or speaker-dependent, in which case the interface and computer may be used for voice-training purposes.

One or more microphones may be provided to capture speech from the user for control purposes, including microphone 1016 mounted on the head unit 1002, and/or one or more remote mics 1018, which may mounted on eyeglass frames, a headband, or support arm to bring the mic closer to the mouth of a user.

In a most basic configuration, the user would be able to turn the headlamp on and off with respective spoken commands "ON" and "OFF." To avoid false commands and provide for other functions as described below, a preamble may be used, such as "LIGHT—ON" and "LIGHT—OFF." If brightness control is provided, commands such as "LIGHT—BRIGHTER" and "LIGHT—DIMMER" may be used.

In addition to voice-activated headlamp control, the invention may be used to control other accessories such as video camera 1030, in which case commands such as "CAMERA—ON," "CAMERA—OFF," "CAMERA—ZOOM IN(/OUT)," "CAMERA—FOCUS," and so forth. Although FIG. 10 shows the camera connected to the head-mounted unit 1002 to use controller 1012, the voice-activated camera controls may be provided in unit 1030 with or without a headlamp.

As mentioned, the voice-activated control may be used with or without an I.R. sensor 1014. One use for both is in setting threshold control. For example, a user may place her hand at a particular distance from sensor 1014, and speak the command(s) "LIGHT—ON" or "LIGHT—OFF" to set the distance the user wants to turn the light on and/or off using their hand. A user may place their hand at a desired distance from the sensor 1014 and speak "CAMERA—FOCUS" to set a particular focus point for a video camera.

Figure 11:
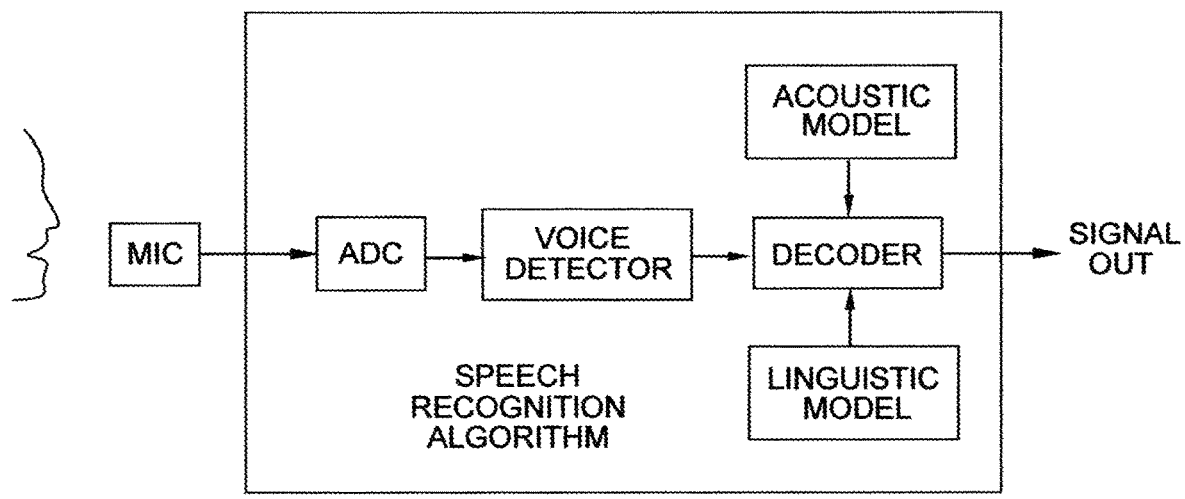
FIG. 11 is a block diagram of voice-activated components and algorithms applicable to the invention.

FIG. 11 is a block diagram specific to voice-activated components applicable to the invention. Specifically, the voice of a user is detected by a microphone, and an electrical signal representative of the user's speech is converter from analog to digital form by the A-D converter. The digitized signal is delivered to a voice detector which may receive inputs from both an acoustic model and a linguistic model. After the speech is recognized, a signal is output through a decoder, enabling the speech to function as a command in accordance with this invention.

The invention claimed is:
1. A voice-activated headlamp, comprising:
    a battery unit;
    a head-mounted unit, including:
        a light source;
        a power switch receiving power from the battery unit;
        a microphone; and
        a controller operative to perform the following functions:
            (a) receive an electrical signal from the microphone representative of a voice command; and
            (b) send a signal to the power switch to control the light source in accordance with the voice command;
    wherein the voice command includes turning the light source ON or OFF; and
    wherein the battery unit provides fixed-voltage power signals to the head-mounted unit such that no control signals are required from the head-mounted unit to the battery unit.
2. The voice-activated headlamp of claim 1, wherein the light source is a light-emitting diode (LED).
3. The voice-activated headlamp of claim 1, wherein the microphone is mounted on the same head-mounted unit that includes the light source.

4. The voice-activated headlamp of claim 1, wherein the head-mounted unit includes an interface for receiving a voice command from a remote microphone.

5. The voice-activated headlamp of claim 1, wherein the battery unit is physically coupled directly to the head-mounted unit.

6. The voice-activated headlamp of claim 1, wherein the head-mounted unit includes an interface for receiving power from a remote battery unit.

7. The voice-activated headlamp of claim 1, wherein the head-mounted unit includes an interface to a computer for voice-command training.

8. The voice-activated headlamp of claim 1, wherein the head-mounted unit includes a memory for storing the voice commands.

9. The voice-activated headlamp of claim 1, wherein:
the head-mounted unit includes an interface to a video camera;
the controller is further operative to control the video camera in accordance with a voice command; and
the voice command includes turning the video camera ON or OFF.

10. The voice-activated headlamp of claim 9, wherein the controller is further operative to control the focus or zoom of the video camera in accordance with a voice command.

11. The voice-activated headlamp of claim 1, further including a proximity sensor to assist in controlling the light source.

12. The voice-activated headlamp of claim 11, wherein the proximity sensor assists in setting an ON or OFF threshold of the light source.

13. The voice-activated headlamp of claim 11, wherein the proximity sensor is an active infrared (IR) sensor including an IR emitter and an IR detector.

14. The voice-activated headlamp of claim 1, wherein the power switch receives a fixed-voltage power signal directly from the battery unit.

15. The voice-activated headlamp of claim 1, including a mechanism to attach the head-mounted unit to eyeglass frames.

16. The voice-activated headlamp of claim 1, wherein the power switch is a FET switch.

17. The voice-activated headlamp of claim 1, including a mechanism to attach the head-mounted unit to a headband.

18. A voice-activated headlamp, comprising:
a battery unit;
a head-mounted unit, including:
a light source;
a power switch receiving power from the battery unit;
a microphone; and
a controller operative to perform the following functions:
(c) receive an electrical signal from the microphone representative of a voice command; and
(d) send a signal to the power switch to control the light source in accordance with the voice command;
wherein the voice command includes turning the light source ON or OFF; and
wherein the power switch receives a fixed-voltage power signal directly from the battery unit.

19. The voice-activated headlamp of claim 18, wherein the light source is a light-emitting diode (LED).

20. The voice-activated headlamp of claim 18, wherein the microphone is mounted on the same head-mounted unit that includes the light source.

21. The voice-activated headlamp of claim 18, wherein the head-mounted unit includes an interface for receiving a voice command from a remote microphone.

22. The voice-activated headlamp of claim 18, wherein the battery unit is physically coupled directly to the head-mounted unit.

23. The voice-activated headlamp of claim 18, wherein the head-mounted unit includes an interface for receiving power from a remote battery unit.

24. The voice-activated headlamp of claim 18, wherein the head-mounted unit includes an interface to a computer for voice-command training.

25. The voice-activated headlamp of claim 18, wherein the head-mounted unit includes a memory for storing the voice commands.

26. The voice-activated headlamp of claim 18, wherein:
the head-mounted unit includes an interface to a video camera;
the controller is further operative to control the video camera in accordance with a voice command; and
the voice command includes turning the video camera ON or OFF.

27. The voice-activated headlamp of claim 26, wherein the controller is further operative to control the focus or zoom of the video camera in accordance with a voice command.

28. The voice-activated headlamp of claim 18, further including a proximity sensor to assist in controlling the light source.

29. The voice-activated headlamp of claim 28, wherein the proximity sensor assists in setting an ON or OFF threshold of the light source.

30. The voice-activated headlamp of claim 28, wherein the proximity sensor is an active infrared (IR) sensor including an IR emitter and an IR detector.

31. The voice-activated headlamp of claim 18, wherein the battery unit provides fixed-voltage power signals to the head-mounted unit such that no control signals are required from the head-mounted unit to the battery unit.

32. The voice-activated headlamp of claim 18, including a mechanism to attach the head-mounted unit to eyeglass frames.

33. The voice-activated headlamp of claim 18, wherein the power switch is a FET switch.

34. The voice-activated headlamp of claim 18, including a mechanism to attach the head-mounted unit to a headband.

* * * * *